Figure 1:
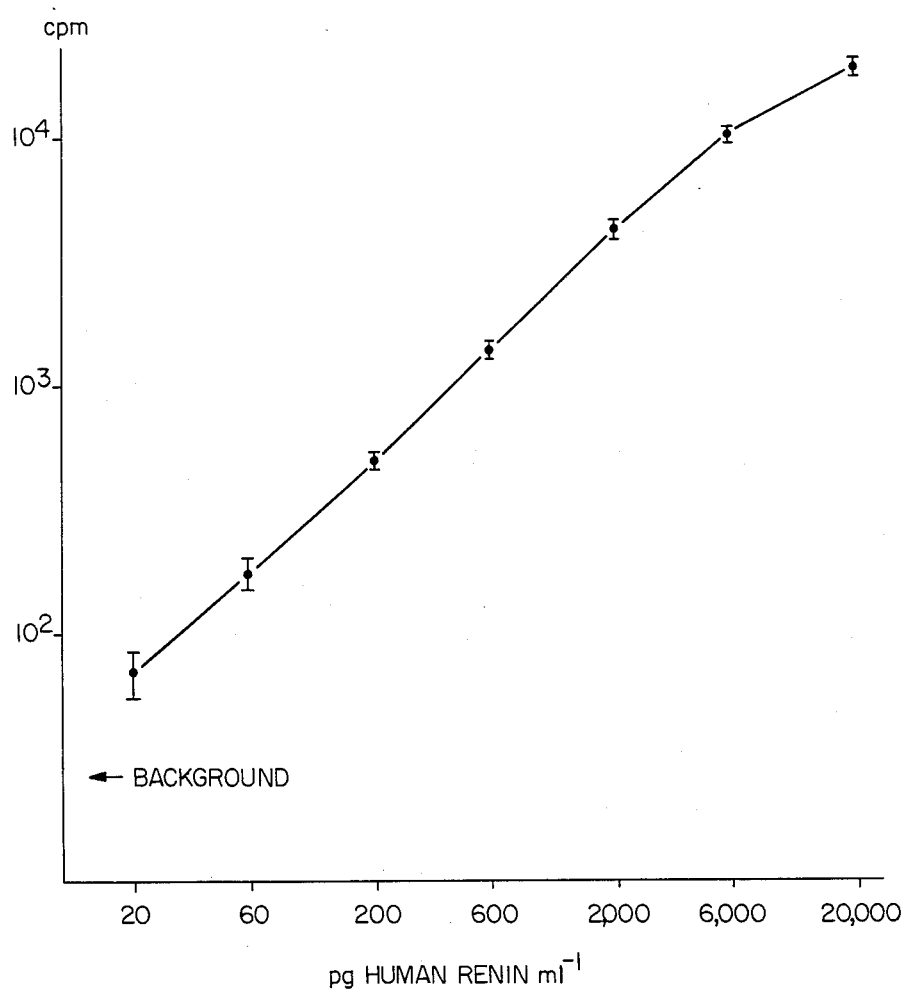

United States Patent [19]

Heusser et al.

[11] Patent Number: 4,780,401
[45] Date of Patent: Oct. 25, 1988

[54] NOVEL MONOCLONAL ANTIBODIES TO HUMAN RENIN AND HYBRIDOMA CELLS, PROCESSES FOR THEIR PREPARATION AND THEIR APPLICATIONS

[75] Inventors: Christoph Heusser, Bottmingen; Rudolf H. Andreatta, Allschwil; Sefik Alkan, Riehen; Jeanette Wood, Biel-Benken, all of Switzerland

[73] Assignee: Ciba-Geigy Corporation, Ardsley, N.Y.

[21] Appl. No.: 717,738

[22] Filed: Mar. 28, 1985

[30] Foreign Application Priority Data

Apr. 9, 1984 [CH] Switzerland ............... 1781/84

[51] Int. Cl.⁴ ............... G01N 33/53; G01N 33/577; C12N 15/00
[52] U.S. Cl. ............... 435/7; 435/68; 435/172.2; 435/810; 424/85.8; 424/88; 436/518; 436/548; 436/808; 436/815; 530/387; 530/388; 530/808; 935/89; 935/93; 935/104; 935/106; 935/107; 935/108; 935/110
[58] Field of Search ............... 435/7, 68, 172.2, 948, 435/810; 424/85, 88; 436/501, 518, 548, 815, 808; 530/387, 388, 808, 809; 935/89, 93, 106, 104, 107, 108, 110

[56] References Cited

U.S. PATENT DOCUMENTS

4,376,110 3/1983 David et al. ............... 436/548

OTHER PUBLICATIONS

Slater, E. E., et al, Journ. Biol. Chem., 256 No. 15: 8164–8171 (1981).
Galen et al., J. Clin. Invest., vol. 74(3), pp. 723–735, (1984) (abstract only).
Corvol et al, Chemical Abstracts, vol. 102(13) No. 108589n (1984).
Menard et al, Chemical Abstracts, vol. 103(7), No. 50128p (1984).
Michel, et al. Amer. Journal of Physiology, vol. 15, No. 3 (3/84) pp. F309.
Heterogeneity of Renin and Renin–Substrate (ed. M. P. Sambhi), Elsevier North Holland Inc., pp. 237–241 (1981)—Soubrier et al.
Pau et al, Clin. Sci. 61, 239 (1981).
H. Clin. Endocr. Met., 48, 1041 (1979)—Galen et al.
J. Hypertens., 2 (Suppl. 3), 275–278 (1984)—Menard et al.
Proc. Int. Symp. Radioimmunol., 6, 69–79 (1984)—Corvol et al.
D. Simon et al. J. Clin. Endocr. Met., vol. 53 (1981), pp. 453–455.
V. J. Dzau et al., Clin. and Exper. Hyper. A5 (1983), pp. 1207–1220.

*Primary Examiner*—Robert J. Warden
*Assistant Examiner*—Jack Spiegel
*Attorney, Agent, or Firm*—Irving N. Feit; Meredith C. Findlay

[57] ABSTRACT

The invention relates to novel monoclonal antibodies having a high affinity for human renin, derivatives thereof, processes for the preparation of these antibodies and their derivatives, hybridoma cell lines that produce these antibodies, and to processes for the preparation of said hybridoma cells lines. The monoclonal antibodies according to the invention and their derivatives can be used for the qualitative and quantitative determination of human renin and structurally similar renin, for the purification of human renin and structurally similar renin and for the treatment of high blood pressure and cardiac insufficiency.

13 Claims, 2 Drawing Sheets

NOVEL MONOCLONAL ANTIBODIES TO HUMAN RENIN AND HYBRIDOMA CELLS, PROCESSES FOR THEIR PREPARATION AND THEIR APPLICATIONS

The invention relates to novel monoclonal antibodies having a high affinity for human renin, derivatives thereof, processes for the preparation of these antibodies and their derivatives, hybridoma cell lines that produce these antibodies, processes for the preparation of said hybridoma cell lines, the use of the monoclonal antibodies and their derivatives for the qualitative and quantitative determination of human renin and structurally similar renin, test kits therefor, the use of the monoclonal antibodies and their derivatives for the purification of human renin and structurally similar renin, pharmaceutical preparations containing said antibodies or derivatives thereof and to the use of the monoclonal antibodies and their derivatives for the treatment of high blood pressure and cardiac insufficiency.

BACKGROUND TO THE INVENTION

Renin is a proteolytic enzyme that, by releasing the angiotensins, plays a part in the regulation of the blood pressure. Human renin is a glycosylated protein having a molecular weight of approximately 40,000. Some structural characteristics of human renin are known. For example, the amino acid sequence of the polypeptide has been clarified by determining the complementary deoxyribonucleic acid (cDNA) that codes for renin. Renin is released in the kidneys from an inactive form, pro-renin, and then passes into the blood stream where it is to be found in concentrations of from 20 to 100 pg/ml. There, it brings about the cleavage of angiotensinogen (renin substrate) to form the decapeptide angiotensin I which in turn is cleaved by the so-called angiotensin-converting enzyme (ACE) in the lungs, kidneys and other organs to form the octapeptide angiotensin II. Angiotensin II raises the blood pressure both directly through arterial constriction and indirectly by releasing from the adrenal glands the hormone that causes sodium-retention, aldosterone, which is associated with an increase in the extracellular fluid volume. Angiotensin II is broken down by angiotensinases to the heptapeptide angiotensin III, which exhibits actions similar to those of angiotensin II, and to smaller, inactive fragments.

The treatment of certain forms of high blood pressure (hypertension) and cardiac insufficiency is possible by influencing the renin-angiotensin system. A lowering of blood pressure can be achieved by (a) inhibiting the action of angiotensin II (or III) on its receptors, (b) inhibiting the angiotensin-converting enzyme or (c) inhibiting the action of renin on angiotensinogen. Renin-inhibitors are, for example, pepstatin and pepstatin analogues, angiotensinogen analogues and renin antibodies. Such renin-inhibitors reduce the release of angiotensin I from angiotensinogen and thereby lessen also the concentration of the active peptide hormone angiotensin II. Compared with the known renin-inhibitors, the renin antibodies according to the invention have the advantage of inhibiting the action of renin quite specifically even in extremely low concentrations.

The use of antibodies in diagnosis and therapy was, until recently, severely limited in its range of application. Antibodies were obtained in very small amounts from animal serum in the form of a complex mixture of various proteins. Standardisation of the antibodies was not possible since each immunised individual animal, and even a single individual when immunised repeatedly, produces a serum with antibodies of a different composition in each case. By using a new technique developed by Köhler and Milstein [1] it has now become possible to obtain reproducibly in theoretically unlimited quantities antibodies in homogeneous form from cell cultures, that is to say so-called monoclonal antibodies. By fusion of suitable myeloma cells with antibody-producing lymphocytes from a donor immunised with antigen, hybridoma cells are produced which combine the ability to undergo unlimited cell division and unlimited growth in vitro with the production of a homogeneous antibody. Hence, it is possible to render independent the immune response of an organism to a specific antigen and to prepare monoclonal antibodies by continuous culturing of hybrid cells.

Although many examples of the preparation of specific monoclonal antibodies by the hybridoma technique have so far become known and the general procedure has been described in principle, with each new example specific problems arise that require adaptation of the technique to the particular case. Without such adaptation there is no certainty that the desired hybridoma cells will ever be formed, that they will be genetically stable and produce the desired monoclonal antibodies, and that the antibodies so prepared will have the desired specificity. The degree of success is influenced in principle by the type and purity of the antigen used for immunisation of the lymphocyte-donor, the method of immunisation, the technique of cell fusion, the procedure in the selection of suitable hybridoma cell lines and the way in which the monoclonal antibodies are isolated and purified.

Monoclonal antibodies that bind human renin are known. Simon et al. [2] describe a monoclonal antibody having a low affinity for human renin. Dzau et al. [3] describe monoclonal antibodies that bind human renin and simultaneously inhibit the enzymatic function thereof. For the determination of human renin in blood, basically, two different methods are used [4]. In one of these, the enzymatic activity of human renin in plasma is measured by determining the amount of angiotensin I released from angiotensinogen. A measure of the total amount of renin is then obtained by determining the enzymatic activity after activation of inactive plasma renin, for example by treatment with acid at pH 3 to 4. Although this indirect method allows the measurement of renin in low concentrations, it is subject to great uncertainties. In the other method, human renin is determined in immunoassays with the aid of the known monoclonal antibodies or with polyclonal antibodies from serum. This direct method, however, has not hitherto had sufficient sensitivity for a reliable measurement of the extraordinarily low concentrations of human renin in plasma. There is therefore a need for monoclonal antibodies that bind human renin considerably more strongly than do the known antibodies, so that they can be used in immunoassays to give an accurate determination of renin in human blood plasma. There is also a need for monoclonal antibodies that inhibit the action of the enzyme renin so efficiently that they can be used for the treatment of high blood pressure. The present invention represents a solution to this problem in that it provides monoclonal antibodies that bind human renin strongly and, at the same time, efficiently inhibit the enzymatic function thereof.

DESCRIPTION OF THE INVENTION

The invention relates to monoclonal antibodies to human renin and structurally similar renin, and to derivatives thereof, characterised by a high affinity for human renin.

Monoclonal antibodies to human renin can be characterised by the binding constants to surface-bound or dissolved human renin, the inhibiting concentration of the enzyme activity of human renin, the cross-reactivity towards related antigens, for example towards renin of other species, the immunoglobulin class or subclass, and by the N-terminal amino acid sequence of the polypeptide chains.

The invention relates especially to monoclonal antibodies and derivatives thereof that, at a concentration of $3 \times 10^{-10}$M (mol/liter) or less, bind significantly to surface-bound human renin, monoclonal antibodies and derivatives thereof that, at a concentration of $3 \times 10^{-10}$M, bind at least 50% of dissolved human renin that has been added in a limiting amount, and monoclonal antibodies and derivatives thereof that, at a concentration of $2 \times 10^{-8}$M, inhibit the enzyme activity of human renin by at least 50%. Preferred are monoclonal antibodies and derivatives thereof that, at a concentration of $2 \times 10^{-9}$M, inhibit the enzyme activity of human renin by at least 50%. Most especially preferred are monoclonal antibodies and derivatives thereof that, at a concentration of $5 \times 10^{-11}$M, inhibit the enzyme activity of human renin by at least 50%.

An example of a most especially preferred monoclonal antibody is the antibody designated R 3-36-16 which is produced by the cell line R 3-36-16. Monoclonal antibodies R 3-36-16 are gamma 1 kappaimmunoglobulins that contain in the first hypervariable region of the light polypeptide chain, in position 28-38 of the N-terminus, the amino acids $^{28}$serine-$^{29}$valine, $^{31}$serine-$^{32}$tyrosine-$^{33}$glycine-$^{34}$lysine and $^{36}$phenylalanine-$^{37}$methionine.

Derivatives of monoclonal antibodies according to the invention are, for example, fragments, such as Fab, Fab' or F(ab')$_2$ fragments, that retain their specificity for the antigenic determinants of human renin, radioactively labelled monoclonal antibodies which are labelled, for example, with radioactive iodine ($^{125}$I, $^{131}$I), carbon ($^{14}$C), sulphur ($^{35}$S), tritium ($^3$H) or the like, or monoclonal antibody conjugates with enzymes such as horseradish peroxidase, alkaline phosphatase, $\beta$-D-galactosidase, glucose oxidase, glucoamylase, carbonic anhydrase, acetylcholineesterase, lysozyme, malate dehydrogenase or glucose-6-phosphate dehydrogenase. Preferred derivatives are monoclonal antibodies labelled with $^{125}$iodine and monoclonal antibody conjugates with alkaline phosphatase.

The monoclonal antibodies according to the invention and derivatives thereof are obtained according to processes that are known per se as follows: hybridoma cells producing such monoclonal antibodies (a) are cultured in vitro and the monoclonal antibodies are isolated from the culture supernatants, or (b) are multiplied in vivo in a suitable mammal and the monoclonal antibodies are isolated from the body fluids of that mammal, and, if desired, (c) a resulting monoclonal antibody is converted into a derivative thereof.

Suitable culture media for the in vitro culturing according to process (a) are the customary standard culture media, for example Dulbecco's Modified Eagle Medium or RPMI 1640 medium supplemented by fetal calf serum. For isolation of the monoclonal antibodies, the proteins in the culture supernatants are precipitated with ammonium sulphate or the like and purified by the customary chromatography methods, for example gel filtration, ion-exchange chromatography, chromatography over DEAE-cellulose or immuno-affinity chromatography.

Large quantities of the desired monoclonal antibodies can be obtained by multiplying the hybridoma cells in vivo according to process (b). For this purpose, cell clones are injected into syngeneic mammals, and, after 1-3 weeks, the antibodies are isolated from the body fluids of those mammals. For example, hybridoma cells originating from Balb/c mice are injected intraperitoneally into Balb/c mice that have optionally been pretreated with a hydrocarbon such as pristane, and, after 8-10 days, ascitic fluid is taken from these animals. The desired monoclonal antibodies are isolated from the body fluids according to methods that are known per se, for example by precipitation with ammonium sulphate or the like and purification by chromatography, for example over DEAE-cellulose or ion-exchange resin, by gel filtration or immuno-affinity chromatography.

Fragments of monoclonal antibodies according to the invention, for example Fab, Fab' or F(ab')$_2$ fragments, that retain their specificity for the antigenic determinants of human renin are prepared according to methods that are known per se, for example by treating monoclonal antibodies prepared according to process (a) or (b) with enzymes such as pepsin or papain and/or by cleavage of disulphide bonds by chemical reduction.

Monoclonal antibodies radioactively labelled with iodine ($^{125}$I, $^{131}$I) are obtained from the monoclonal antibodies according to the invention by iodination known per se, for example with radioactive sodium or potassium iodide and a chemical oxidising agent, such as sodium hypochlorite, chloramine T or the like, or an enzymatic oxidising agent, such as lactoperoxidase, glucose oxidase and glucose. Radioactively labelled monoclonal antibodies according to the invention are also prepared by adding to the culture media for the in vitro culturing, in a manner known per se. radioactively labelled nutrients containing radioactive carbon ($^{14}$C), tritium ($^3$H), sulphur ($^{35}$S) or the like, for example L-($^{14}$C)-leucine, L-($^3$H)-leucine or L-($^{35}$S)-methionine, and obtaining the monoclonal antibodies according to process, (a).

Enzyme-labelled monoclonal antibodies according to the invention are obtained according to methods that are known per se by reacting monocoonal antibodies prepared according to process (a) or (b) and the desired enzyme with a coupling reagent, for example glutaraldehyde, periodate, N,N'-o-phenylenedimaleimide, N-(m-maleimidobenzoyloxy)-succinimide, N-(3-(2'-pyridyldithio)-propionoxy)-succinimide or the like.

The invention relates also to hybridoma cell lines, characterised in that they produce monoclonal antibodies having a high affinity for human renin. The invention relates especially to cell lines that produce monoclonal antibodies that, at a concentration of $3 \times 10^{-10}$M (mol/liter), bind at least 50% of human renin that has been added in a limiting amount and/or that, at a concentration of $2 \times 10^{-8}$M, inhibit the enzyme activity of human renin by at least 50%. Preferred are cell lines that produce monoclonal antibodies that, at a concentration of $3 \times 10^{-10}$M, bind at least 50% of human renin and/or that, at a concentration of $2 \times 10^{-9}$M, inhibit the enzyme activity of human renin by at least 50%. Most especially preferred are cell lines that produce monoclonal antibodies that, at a concentration of $5\times 10^{-11}$M, inhibit the enzyme activity of human renin by at least 50%.

An example of a most especially preferred hybridoma cell line that produces monoclonal antibodies of high affinity is the cell line designated R 3-36-16 which was deposited on 7.11.1983 at the "Collection Nationale de Cultures de Microorganismes" of the Institut Pasteur in Paris under number I-253. Hybridoma cell line R 3-36-16 is a hybrid of the mouse myeloma cell line Sp2/0-Ag14 and a B-lymphocyte of the spleen of a Balb/c mouse. R 3-36-16 is a stable cell line that secretes monoclonal antibodies of constant specificity and that can be activated from deep-frozen cultures by thawing and recloning.

The invention relates also to a process for the preparation of hybridoma cells that produce monoclonal antibodies having a high affinity for human renin, characterised in that suitable mammals are immunised with purified human renin, antibody-producing cells taken from the mammal are fused with myeloma cells, the resulting hybridoma cells are cloned and those cell clones which produce the desired monoclonal antibodies having a high affinity for human renin are selected.

Immunisation with high-purity human renin is preferred. Such human renin can be obtained, for example, in a manner known per se, from extracts of human kidneys with the aid of immuno-affinity chromatography.

Preferred mammals for immunisation are mice, especially Balb/c mice, but other mouse strains may also be used. The immunisations are performed in a manner known per se, for example by administering parenterally, for example intraperitoneally, intravenously and/or subcutaneously, three to six injections each containing from 1 µg to 20 µg of purified human renin, at intervals of from one to six weeks, preferably together with an adjunct that stimulates the production of lymphocytes, for example complete or incomplete Freund's adjuvant.

Antibody-producing cells of the immunised animals, preferably spleen cells, are taken from the animals two to six days after the last ("booster") immunisation and fused with myeloma cells of a suitable cell line in the myeloma cell lines and cell lines derived therefrom are known as suitable fusion partners. Preferred are myeloma cells that lack the enzyme hypoxanthine-guanine-phosphoribosyl transferase (HGPRT) or the enzyme thymidine kinase (TK) and that, for that reason, do not survive in a selective culture medium containing hypoxanthine, aminopterin and thymidine (HAT medium). Especially preferred are myeloma cells and cell lines prepared therefrom that do not survive in HAT medium and do not secrete any immunoglobulins or parts thereof, for example the cell lines X63-Ag8.653 and Sp2/0-Ag14. As fusion-promoters there come into consideration Sendai virus or other paramyxoviruses, optionally in UV-inactivated form, calcium ions, surface-active lipids, such as iysolecithin, or polyethylene glycol. Myeloma cells are preferably fused with a three- to twenty-fold excess of spleen cells from immunised animals in a solution containing from 30 to 50% polyethylene glycol having a molecular weight of from 1000 to 4000.

After fusion, the cells are portioned out and cultured in selective HAT medium, with only hybridoma cells surviving since these combine, from the myeloma cells, the ability to grow in vitro and, from the antibody-producing cells of the immunised animals, the missing HGPRT or TK genes and, therewith, the ability to survive in HAT medium.

Suitable culture media for the growth of the hybridoma cells are the customary standard culture media, for example Dulbecco's Modified Eagle Medium or RPMI 1640 medium, supplemented by 10–15% fetal calf serum. At the beginning of cell growth, there are preferably added so-called feeder cells, for example normal mouse peritoneal exudate cells, spleen cells, bone marrow macrophages or the like. At regular intervals, said culture media are supplemented by selective HAT medium to prevent the hybridoma cells from being overgrown by ordinary myeloma cells.

The cell culture supernatants of the hybridoma cells are examined to see whether they contain the desired monoclonal antibodies. Advantageously, the cell supernatants are tested in an immunoassay that not only demonstrates the binding of monoclonal antibodies to surface-bound human renin, but, at the same time, also determines the binding to dissolved human renin and the inhibition of the enzyme activity of human renin. Surprisingly, it was found that monoclonal antibodies that bind well to surface-bound renin inhibit the enzyme activity of renin only slightly. By combining different kinds of test method it is possible to identify hybridoma cells that secrete monoclonal antibodies having both a high binding affinity and a strong enzyme-inhibiting action towards human renin. Such hybridoma cells are cloned in a manner known per se by limiting dilution in order to ensure their uniformity.

The invention relates also to the use of the monoclonal antibodies and their derivatives having a high affinity for human renin for the qualitative and quantitative determination of human renin and structurally similar renin, especially in biological fluids. For example, the monoclonal antibodies and antibody derivatives according to the invention can be used in any of the immunoassays known per se that utilise the binding interactions between antigen (human renin) and monoclonal antibody. Examples of such assays are radioimmunoassays (RIA), enzyme-immunoassays, immunofluorescence tests, latex agglutination or haemagglutination.

The monoclonal antibodies according to the invention can be used as such or in the form of radioactively labelled derivatives on their own or in combination in a radioimmunoassay (RIA). Any of the known modifications of an RIA can be used, for example RIA in homogeneous phase, solid phase RIA or heterogeneous RIA, single RIA or double (sandwich) RIA with direct or indirect (competitive) determination of human renin. There is preferred a single RIA in which a suitable carrier, for example the plastics surface of a titre plate or of a test tube, for example of polystyrene, polypropylene or polyvinyl chloride, glass or plastics beads, filter paper, or dextran, cellulose acetate or nitrocellulose sheets or the like, is coated with a monoclonal antibody or with a mixture of two monoclonal antibodies that recognise different epitopes, by simple adsorption or optionally after activation of the carrier, for example with glutaraldehyde or cyanogen bromide, and incubated with the test solution and a solution of a known amount of human renin that is radioactively labelled with $^{125}$I, and the radioactivity bound to said carrier is determined.

Especially preferred is a sandwich radioimmunoassay in which a carrierccoated with one or two monoclonal antibodies is incubated with the test solution and a solution of a monoclonal antibody radioactively labelled with $^{125}$I, the dissolved monoclonal antobody recognising a different epitope of human renin than does or do the carrier-bound monoclonal antibody or antibodies, and the amount of renin in the test solution is determined by measuring the radioactivity bound to the carrier. FIG. 1 shows the measured radioactivity bound to the carrier in relation to the quantity of human renin in the test solution, as can be measured by the sandwich RIA described in detail in Example 8.4. The sensitivity of the test allows a reliable, quantitative determination of from only 1 pg to more than 100 pg of human renin in 50 μl of test solution in less than 4 hours. The use of the monoclonal antibodies according to the invention having a high affinity for renin therefore renders possible the quantitative determination of human renin at concentrations normally occurring in biological fluids and especially in blood, and hence allows a rapid and reliable diagnosis of renin-induced high blood pressure.

The monoclonal antibodies according to the invention can be used as such or in the form of enzyme-conjugated derivatives on their own or in combination in an enzyme-immunoassay. Such immunoassays include test procedures in which enzyme-labelled monoclonal antibody derivatives according to the invention, enzyme-labelled antibodies known per se that recognise and bind the epitopes of the anti-human renin antibodies according to the invention or other anti-human renin antibodies, or enzyme-labelled human renin are used.

There is preferred an ELISA (enzyme-linked immunoadsorbent assay) in which a carrier as described above for a single RIA test is coated with one or two monoclonal antibodies according to the invention, incubated with a test solution containing human renin and then with a polyclonal serum to human renin, for example rabbit serum, and, finally, the bound antibodies of the polyclonal serum are developed by enzyme-labelled antibodies that recognise and bind to them, and the amount of human renin bound is determined by enzyme substrate reaction. Such an enzyme-labelled antibody is, for example, a phosphatase-labelled goat-anti-rabbit immunoglobulin.

There is most especially preferred an ELISA in which a carrier coated with one or two monoclonal antibodies according to the invention is incubated with a test solution containing human renin and with a solution of a monoclonal antibody according to the invention that is conjugated with an enzyme, the dissolved monoclonal antibody recognising a different epitope of human renin than does or do the carrier-bound monoclonal antibody or antibodies. By an enzyme substrate reaction that results, for example, in a colour change and can be observed by eye or with optical measuring devices, the amount of bound enzyme, which is proportional to the amount of human renin in the test solution, is measured.

Figure 2:
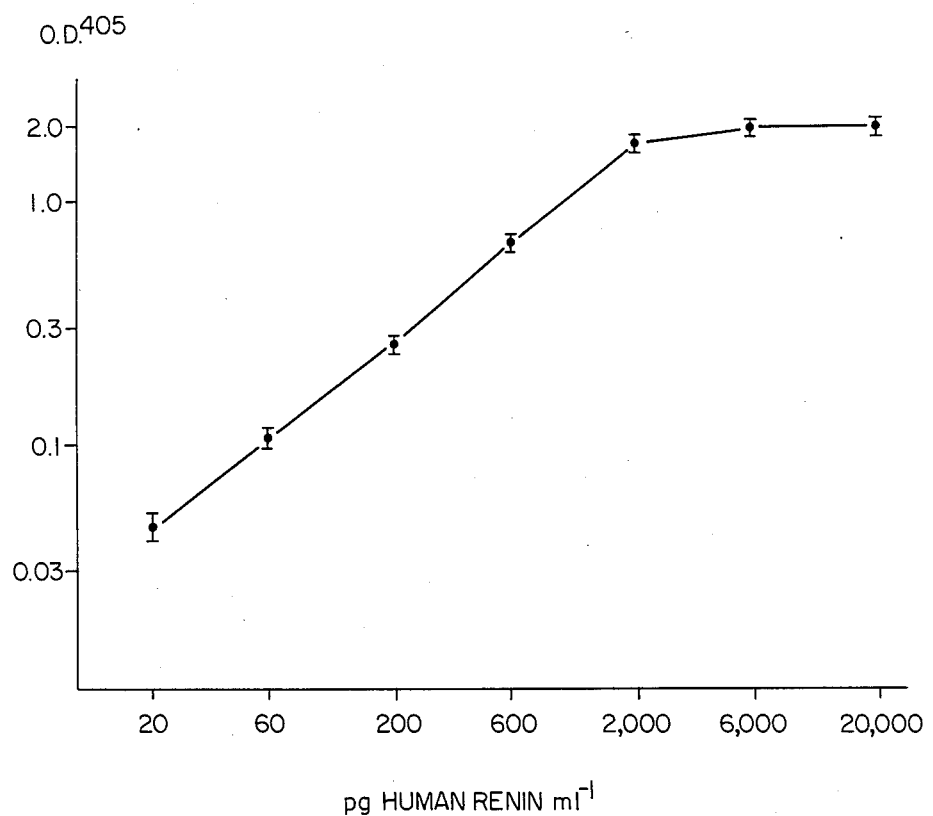

FIG. 2 shows the measured optical density at the maximum extinction of the released coloured enzyme substrate in relation to the amount of human renin in the test solution, as can be measured by the ELISA described in detail in Example 9.3. The sensitivity of the ELISA allows a reliable, quantitative determination of from less than 1 pg up to 100 pg of human renin in 50 μl of test solution in less than 5 hours. Compared with the preferred sandwich RIA described above, the ELISA, with the same or slightly greater sensitivity, has the advantage that no complicated measuring devices are needed as they are for determining radioactivity and that less stringent safety standards have to be met than when dealing with radioactive substances.

Preferred enzymes in the enzyme-immunoassays according to the invention are horseradish peroxidase which can be developed, for example, with the enzyme substrates 5-aminosalicylic acid, o-phenylenediamine, 3,3'-dimethoxybenzidine, 2,2'-azino-bis-(3-ethylbenzothiazolin-6-sulphonic acid) or the like, and especially alkaline phosphatase which, for example, releases p-nitrophenol from the enzyme substrate p-nitrophenyl phosphate.

The use according to the invention of monoclonal antibodies having a high affinity for human renin for the qualitative and quantitative determination of human renin also includes other immunoassays known per se, for example immunofluorescence tests using antibody conjugates or antigen conjugates with fluorescing substances, latex agglutination with antibody-coated or antigen-coated latex particles or haemagglutination with antibody-coated or antigen-coated red blood corpuscles or the like.

The immunoassays described can be used to determine the quantity of human renin in biological fluids, especially in human blood, and hence for the diagnosis of renin-induced high blood pressure. In these immunoassays, there is measured not only that amount of human renin which as the active enzyme converts angiotensinogen (renin substrate) into angiotensin I, but also all other forms of human renin having the same antigenic determinants that are recognised by the antibody. In particular, the described immunoassays determine the total amount of human renin, which includes active enzyme and inactive human renin or human pro-renin. The immunoassays can also be applied to the determination of primate renin, especially renin of marmosets (*Callithrix jacchus*), or other animal renin that has similar or identical antigenic determinants.

The invention relates also to test kits for the determination of human renin and structurally similar renin, containing monoclonal antibodies having a high affinity for human renin and/or derivatives thereof and, optionally, adjuncts.

Test kits according to the invention for a radioimmunoassay contain, for example, a suitable carrier, optionally freeze-dried or concentrated solutions of one or more monoclonal antibodies according to the invention, solutions of a radioactively labelled monoclonal antibody according to the invention or of radioactively labelled human renin, standard solutions of human renin, buffer solutions and, optionally, detergents for preventing non-specific adsorption and aggregate formation, pipettes, reaction vessels, calibration curves and the like.

Test kits according to the invention for an enzyme-immunoassay contain, for example, a suitable carrier, optionally freeze-dried or concentrated solutions of one or more monoclonal antibodies according to the invention, optionally freeze-dried or concentrated solutions of an enzyme-labelled monoclonal antibody according to the invention, of enzyme-labelled human renin, of a polyclonal anti-human renin serum and/or of enzyme-labelled monoclonal or polyclonal antibodies that recognise and bind the anti-human renin antibodies according to the invention or other anti-human renin antibodies, enzyme substrates in solid or dissolved form, standard solutions of human renin, buffer solutions, detergents, pipettes, reaction vessels, calibration curves, colour scale tables and the like.

The invention relates also to the use of the monoclonal antibodies and their derivatives having a high affinity for human renin for the purification of human renin and structurally similar renin. For example, human renin or structurally similar renin can be purified using separating methods known per se, the separating action of which is based on binding interactions between monoclonal antibodies and antigenic determinants of renin. A preferred separating method is immuno-affinity chromatography. A suitable carrier material on an inorganic or organic basis, for example cross-linked agarose, dextran or polyacrylamide in suitably functionalised form, is charged in a manner known per se, optionally having been activated, with the monoclonal antibodies or antibody derivatives according to the invention. For this purpose, for example, a carrier material containing activated ester functions is suspended in an aqueous buffer solution, mixed with a solution of the monoclonal antibody, then unbound monoclonal antibodies are washed out and unoccupied reactive sites of the carrier material are blocked.

The invention relates also to pharmaceutical preparations containing a monoclonal antibody having a high affinity for human renin or a derivative thereof and, optionally, pharmaceutical adjuncts. Suitable derivatives are fragments of monoclonal antibodies, for example Fab, Fab' or F(ab')$_2$ fragments, that have retained their specificity for the antigenic determinants of human renin. The pharmaceutical preparations contain, for example, monoclonal antibodies or fragments thereof in an effective amount together or in admixture with inorganic or organic, solid or liquid pharmaceutically acceptable carriers.

There are preferred pharmaceutical preparations for parenteral, for example intramuscular or, especially, intravenous administration. Such preparations are isotonic aqueous solutions or suspensions which, if desired, are not prepared until just before use, from lyophilised preparations or concentrated solutions. The pharmaceutical preparations may be sterilised and/or contain adjuncts, for example preservatives, stabilisers, wetting agents and/or emulsifiers, solubilisers, salts for regulating the osmotic pressure and/or buffers, and are produced in a manner known per se, for example by means of conventional dissolving or lyophilising processes. The solutions or suspensions mentioned may contain substances that increase the viscosity, such as sodium carboxymethylcellulose, dextran, polyvinylpyrrolidone or gelatine.

Injection preparations are produced in customary manner under antimicrobial conditions, as is the introduction thereof into ampoules or vials and the sealing of the containers.

The invention relates also to the use of the monoclonal antibodies having a high affinity for human renin or derivatives thereof for the treatment of high blood pressure and cardiac insufficiency.

In order to detect the blood pressure-reducing action of the monoclonal antibodies according to the invention, an in vivo test on marmosets (*Callithrix jacchus*) is used. The monoclonal antibodies according to the invention inhibit marmoset renin to approximately the same extent as human renin, that is to say recognise and bind antigenic determinants that are similar or identical in marmoset renin and human renin.

In a customary test procedure, normotensive marmosets (*Callithrix jacchus*) of both sexes having a body weight of approximately 300 g are fed with a normal salt diet (NAFAG, Na$^+$: 100 mmol/kg, K$^+$: 250 mmol/kg) supplemented by fruit. The endogenous release of renin is stimulated by an intravenous injection of furosemide (5 mg/kg). 45 minutes later, the monoclonal antibodies are injected into the lateral caudal vein via a catheter and their effect on the blood pressure and heart rate is measured by means of a catheter in the femoral artery. 2 hours after the injection of the monoclonal antibodies, teprotide, which inhibits the angiotensin-converting enzyme (ACE), is injected (1 mg/kg i.v.) and its effect on the blood pressure is observed. In control experiments, physiological saline solution (1 ml/kg) or the non-specific monoclonal myeloma antibody MOPC 21 (0.1 mg/kg) is injected instead of the monoclonal anti-human renin antibodies according to the invention.

Under these test conditions, a single injection of the monoclonal antibody R 3-36-16 at a dosage of 0.01 mg/kg i.v. reduces the blood pressure by 18±5 mm Hg (n=4) for a duration of up to 2 hours without altering the heart rate. For 30 minutes, the plasma renin activity is completely inhibited. The injection of teprotide after the administration of antibodies does not bring about any additional lowering of the blood pressure. Higher doses of monoclonal antibody R 3-36-16 (0.1 mg/kg i.v.) have a similar blood pressure-reducing action without affecting the heart rate, and lower doses (0.001 mg/kg i.v.) have no effects.

The following Examples illustrate the invention described above but do not limit the scope thereof in any way.

The abbreviations used in the Examples have the following meanings:
BSA: bovine serum albumin
ELISA: enzyme assay (enzyme-linked immunoadsorbent assay)
HAT: hypoxanthine/aminopterin/thymidine
IC 50: concentration at which 50% inhibition is observed
PBS: phosphate buffered physiological saline solution
RIA: radioimmunoassay
SDS: sodium dodecyl sulphate
tris: tris-(hydroxymethyl)-aminomethane
units:
M: mol/liter
GU: Goldblatt units
cpm: count per minute (radioactive decay)

EXAMPLE 1

Purification of human renin

Human renin is obtained from human kidneys and purified in a manner known per se with the aid of the immuno-adsorption technique.

1 kg of mechanically chopped kidney is extracted with water and acidified to pH 2.8 with sulphuric acid. The NaCl concentration is adjusted to 0.8M and the renin is precipitated with ammonium sulphate (final concentration 2.3M). The precipitate is dialysed against 0.1M phosphate buffer (pH 7.4) and has a concentration of 0.13 GU of renin per mg of protein. The renin content is measured by determining angiotensin I after incubation of the sample with an excess of renin-free plasma as the source of angiotensinogen (NEN, New England Nuclear Angiotensin I Radioimmunoassay Kit) and expressed in Goldblatt units (GU) in comparison with a renin standard (MRL, international reference standard 68/356[5]). The protein concentration is determined by colouring with Coomassie blue and comparison with bovine serum albumin (BSA) as the standard.

The dialysed kidney extract is introduced into an immuno-affinity column containing 38 mg of monoclonal anti-human renin antibody F 15 (Clin-Midy, Montpellier) [6] bound to 6 ml of Affi-Gel® 10 (Biorad). Unbound components of the plasma are washed away with 0.1M phosphate buffer and bound renin is eluted with 0.1M citrate/phosphate buffer (pH 4.5). The eluate is concentrated on an Amikon-PM-10® membrane, diluted with PBS (phosphate-buffered saline), frozen and kept at −80° C. In this manner, approximately 70% of the renin present in the crude kidney extract, having a specific activity of 400 GU/mg, are obtained, which corresponds to a 3000-fold enrichment. The purity of the preparation is analysed by SDS-polyacrylamide gel electrophoresis and high pressure liquid chromatography and is estimated to be more than 80%.

EXAMPLE 2

Preparation of the hybridoma cells 2.1 Immunisation of mice with human renin

Balb/c mice are immunised with the purified human renin from Example 1 as follows:

Mouse 1 and 2 receive 10 GU, corresponding to approximately 10 μg of renin, in complete Freund's adjuvant (CFA) distributed between two hind paws and two subcutaneous (s.c.) injections. On the 28th day thereafter, a further 2 GU of renin and, on the 46th day, 5 GU of renin in PBS are injected intravenously (i.v.). The spleen is removed on the 50th day for fusion.

Mouse 3 and 4 receive 20 GU of renin in CFA distributed as for mouse 1 and 2, on the 35th day 2 GU of renin in incomplete Freund's adjuvant (IFA) s.c., on the 60th day 2 GU of renin in PBS intraperitoneally (i.p.) and on the 78th day 5 GU of renin in PBS i.v.. On the 82nd day, the spleen of the mouse having the higher serum titre against in vitro renin activity (mouse 3) is removed for fusion.

2.2 Cell fusion

All the fusion experiments are carried out using the Sp2/0-Ag14 cell line [7] substantially in accordance with the method of Köhler and Milstein [1]. $10^8$ spleen cells from Example 2.1 are mixed with $10^7$ myeloma cells in the presence of 1 ml of 50% strength polyethylene glycol (PEG 1500, Serva). After washing, the cells are resuspended in 48 ml of Standard Dulbecco's Minimum Essential Medium (Gibco No. 0422501). 15% fetal calf serum and $3 \times 10^6$ normal mouse peritoneal exudate cells are added per fusion as feeder cells. The cells are distributed between $48 \times 1$ ml Costar plates. The cultures are fed twice daily with Standard HAT Selective Medium [1] for from 3 to 6 weeks. After the hybrid cells have grown, the culture supernatants are examined for binding to renin (Example 4) and for inhibition of renin activity (Example 5). Cloning of the hybridoma cells is carried out by limiting dilution in microtitre plates. All cells lines are cloned sequentially at least twice.

Clones from ten different mother cultures are selected and grown. R1, R2 and R3 denote hybridoma cells and antibodies obtained therefrom from the fusion of the spleen cells of mouse 1, 2 and 3, respectively. The clone number and any sub-clone number given appear after hyphens (Table 1).

EXAMPLE 3

Isolation and purification of monoclonal antibodies 8-10 week old Balb/c mice (Sisseln animal farm) are pre-treated i.p. with 0.3 ml of pristane (Aldrich). 2-3 weeks later, $2-5 \times 10^6$ cloned hybridoma cells and 0.2 ml of pristane are injected i.p. into each mouse. 8-10 days thereafter, the mice are repeatedly tapped and the ascitic fluid so obtained is centrifuged at 800 g, and the clarified supernatant obtained thus is collected at −20° C.

Thawed ascites solution is centrifuged for 60 minutes at 50,000 g, fat that floats up is removed and a concentration of 10-12 mg of protein per ml is established. The protein concentration is determined by measuring the optical density at 280 nm ($OD_{280}$). A 1% strength solution (w/v) of murine immunoglobulin of $OD_{280}=12$ (1 cm layer thickness) is used as the standard. By slowly adding dropwise 0.9 volume equivalents of saturated ammonium sulphate solution while stirring at 0° C., a crude immunoglobulin fraction is precipitated which is dissolved in 20 mmol of tris-HCl/50 mmol of NaCl (pH 7.9) and dialysed. Two-fold dilution is then carried out with 20 mmol of tris-HCl (pH 7.9) and the whole is introduced into a DEAE-D52 cellulose column (Whatman). The immunoglobulin G-fraction is eluted from the column with a buffer of 20 mmol of tris-HCl/80 mmol of NaCl (pH 7.9) and, after precipitation again with ammonium sulphate (see above), adjusted with PBS to a protein concentration of 10 mg/ml. The purity of the monoclonal antibody preparations is examined using SDS-polyacrylamide gel electrophoresis and is better than 95%.

EXAMPLE 4

Binding of the monoclonal antibodies to human renin 4.1 Enzyme-immunoassay (ELISA)

The reactivity towards surface-bound renin is used in an ELISA method [8] known per se both for the selection of the desired monoclonal antibody-producing hybridoma cells after cell hybridisation (Example 2.2) and for the quantitative determination of the binding to renin in the case of purified monoclonal antibodies. 100 ng of purified renin (Example 1) in 50 μl of 0.05M sodium bicarbonate buffer (pH 9.6) are incubated for 2 hours at 37° C. and for 15 hours at 4° C. in plastics microtitre plates. After washing with PBS, protein-reactive sites that are still present on the plastics surface are saturated by cubation for 2 hours at 37° C. with 150 μl of PBS-Tween® buffer (0.05% Tween® 20 in PBS containing 0.2% $NaN_3$, pH 7.4) and the plates are washed with PBS. 100 μl of the solution to be measured for monoclonal anti-renin antibodies (cell culture supernatants or purified monoclonal antibody solutions) and corresponding dilutions thereof are incubated for 2 hours at 37° C. and, after washing the plates, the bound monoclonal mouse antibodies are developed by incubation with 100 μl of a correspondingly predetermined dilution of a preparation of phosphatase-labelled rabbit IgG anti-mouse immunoglobulin. The amount of enzyme taken up is determined by incubation (30 minutes, 37° C.) with 100 μl of a solution of the enzyme substrate p-nitrophenyl phosphate (1 mg/ml in 10% diethanolamine buffer containing 0.5 mol of $MgCl_2$, pH 9.8) and measurement of the optical density of the reacted product at 405 nm ($OD_{405}$) using a Multiscan Photometer (Flow Irvine, Scotland). As a control, there are used, instead of the solutions containing monoclonal anti-renin antibodies, preparations of the non-specific monoclonal myeloma antibody MOPC 21 (Bionetics Labs., Kensington, U.S.A.) and of a monoclonal hybridoma antibody specific for phosphorylcholine.

The concentration of purified monoclonal antibody, which in this assay with surface-bound human renin finally gives an $OD_{405}$ of 0.1, is listed in Table 1. The concentrations found are within the range of from $5.8 \times 10^{-7}$ to $7.5 \times 10^{-11}$M, concentrations greater than $10^{-7}$M not representing any specific binding since the monoclonal control antibodies in the assay also give values of that order of magnitude. Especially efficient binding to fixed renin (ELISA) is found in the case of the monoclonal antibodies R 3-17-7 and R 3-17-8, but the monoclonal antibodies R 3-48, R 3-21 and R 3-27 also bind at concentrations below $5 \times 10^{-10}$M.

4.2 Radioimmunoassay (RIA) with $^{125}$I-labelled renin

In order to determine the reactivity towards soluble renin, there are added to various dilutions of a monoclonal antibody sample in 50 μl of RIA-buffer (1% BSA in PBS, 0.2% $NaN_3$, pH 7.4) 50 μl of $^{125}$I-labelled renin (80,000 cpm corresponding to 2.5 ng of protein, Example 8.1) in the same buffer and incubation is carried out in polyvinyl chloride microtitre plates for 2 hours at 37° C. and for 15 hours at 4° C. The amount of antibody-bound $^{125}$I-renin is obtained by precipitation of the monoclonal antibodies in the form of immune complexes by adding 50 μl of a corresponding dilution of a rabbit-anti-mouse immunoglobulin serum in 3% polyethylene glycol 6000 and incubating for 30 minutes at 37° C. and for 30 minutes at 4° C. The precipitate is washed several times by suspending and centrifuging and the radioactivity is determined in a gamma counter after cutting the titre plates.

The concentration of purified monoclonal antibody that precipitates 50% of the maximum precipitable radioactivity from the $^{125}$I-renin-containing solution (IC 50) is a measure of the binding to dissolved renin and is given in Table 1. The monoclonal antibodies R 3-36-16 and R 3-47 bind dissolved renin especially strongly although, in an ELISA (Example 4.1), they exhibit only slight affinity for surface-bound renin.

EXAMPLE 5

Inhibition of renin activity in vitro 5.1 Determination of the inhibition of human renin activity Renin-depleted normal human plasma containing angiotensinogen is supplemented to 250 pg/ml renin with purified human renin (Example 1). 50 μl in each case of this pre-treated plasma are incubated for 2 hours at 4° C. and for 1 hour at 37° C, with different dilutions of the monoclonal antibody samples in 50 μl of 0.1M trisacetate buffer (pH 7.4) which are to be analysed, in the presence of 2,3-dimercapto-1-propanol and 8-hydroxyquinoline, which block the conversion of angiotensin I into angiotensin II. The enzymatic reaction is stopped by cooling to 4° C. The amount of angiotensin I formed is determined using an RIA (NEN, New England Nuclear Angiotensin I Radioimmunoassay Kit). For this purpose, the samples are provided with $^{125}$I-labelled angiotensin I-tracer and a corresponding amount of antiserum to angiotensin I and, after incubation for 15 hours at 4° C., unbound angiotensin I is adsorbed on active carbon and the antibody-bound $^{125}$I-labelled angiotensin I in the supernatant is determined with a gamma counter. In this system, the positive control (samples without monoclonal antibodies) give 10 ng of angiotensin I per ml per hour.

The concentration of purified monoclonal antibody at which 50% of the maximum obtainable inhibition of human renin activity (IC 50) is observed is indicated in Table 1 and ranges from more than $10^{-6}$M to $1.3 \times 10^{-11}$M. The monoclonal antibodies R 3-17-7 and R 3-48 do not significantly inhibit renin activity, although they bind renin strongly in an ELISA (Example 4.1). The monoclonal antibodies R 1-19, R 1-20, R 3-17-8, R 2-12 and R 3-21 exhibit significant but weak inhibition of renin activity. Pronounced inhibition of the renin activity is observed in the case of the monoclonal antibodies R 3-27, R 2-1 and, especially, R 3-47 and R 3-36-16.

The monoclonal antibodies R 3-21 and R 2-1 inhibit renin by only up to 60% over the entire concentration range investigated (up to $10^{-6}$M), whilst R 3-27 exhibits a maximum inhibition of only 35%. These monoclonal antibodies recognise and bind antigenic determinants (epitopes) that very probably lie in the vicinity of the active centre of renin. By their binding they impair the enzyme activity as a result of steric influence or promote an allosteric configuration of the renin molecule which still permits a smaller substrate exchange number. The monoclonal antibodies R 1-19 and R 1-20 that inhibit only weakly, on the other hand, bring about, in high concentrations, complete renin inhibition exactly like the monoclonal antibodies having the greatest affinity, antibodies R 3-47 and R 3-36-16.

TABLE 1

Reactivity towards human renin[a]

| group | clone designation | antibody class | binding to renin | | inhibition of renin activity (Example 5.1) | |
|---|---|---|---|---|---|---|
| | | | ELISA (Example 4.1) | RIA (Example 4.2) | IC 50 | max. obtainable inhibition (%) |
| 1 | R 3-17-7 | γ1 | $9.5 \times 10^{-11}$ | [b] | $>10^{-6}$ | [b] |
| | R 2-12 | γ2 | $4.2 \times 10^{-9}$ | $1.5 \times 10^{-7}$ | $>10^{-6}$ | [b] |
| | R 3-17-8 | γ1 | $7.5 \times 10^{-11}$ | $4.9 \times 10^{-9}$ | $8.0 \times 10^{-8}$ | [b] |
| | R 3-48 | γ1 | $1.1 \times 10^{-10}$ | $2.1 \times 10^{-8}$ | $8.5 \times 10^{-8}$ | [b] |
| 2 | R 3-21 | γ1 | $1.5 \times 10^{-10}$ | $9.1 \times 10^{-10}$ | $1.4 \times 10^{-9}$ | 60 |
| | R 3-27 | γ1 | $4.8 \times 10^{-10}$ | $5.7 \times 10^{-10}$ | $1.0 \times 10^{-10}$ | 35 |
| | R 2-1 | γ1 | $5.8 \times 10^{-7}$ | $4.1 \times 10^{-9}$ | $5.7 \times 10^{-10}$ | 60 |
| 3 | R 3-36-16 | γ1 | $6.5 \times 10^{-8}$ | $1.7 \times 10^{-10}$ | $1.3 \times 10^{-11}$ | 100 |
| | R 3-47 | γ1 | $8.2 \times 10^{-9}$ | $2.4 \times 10^{-10}$ | $2.0 \times 10^{-11}$ | 100 |
| 4 | R 1-19 | γ1 | $9.3 \times 10^{-8}$ | $2.5 \times 10^{-8}$ | $1.4 \times 10^{-8}$ | 100 |

TABLE 1-continued

| | | Reactivity towards human renin[a] | | | |
|---|---|---|---|---|---|
| | | binding to renin | | inhibition of renin activity (Example 5.1) | |
| group | clone designation | ELISA (Example 4.1) | RIA (Example 4.2) | IC 50 | max. obtainable inhibition (%) |
| | R 1-20 | γ1 | $3.7 \times 10^{-7}$ | $2.0 \times 10^{-8}$ | $1.4 \times 10^{-8}$ | 100 |

[a] concentrations in mol per liter (M)
[b] not determined

5.2 Comparison of the binding to human renin and the inhibition of human renin activity The monoclonal antibodies can be divided with regard to their binding and inhibiting properties into four different groups. In principle, monoclonal antibodies that only bind renin and those that bind renin and simultaneously impair the enzymatic activity thereof are to be expected. Group 1 (Table 1) comprises monoclonal antibodies that bind renin but do not, or only very weakly, inhibit the catalytic activity thereof. These monoclonal antibodies exhibit, in addition, an at least twenty-fold higher affinity for surface-bound renin (ELISA) in comparison with their affinity for renin in solution (RIA). The monoclonal antibodies of all the other groups show no preference for surface-bound renin. Monoclonal antibodies of group 2 inhibit renin activity even at low concentrations but only partially, that is to say only by a certain percentage that is characteristic of the monoclonal antibody. Group 3 comprises monoclonal antibodies that inhibit renin activity completely even at extremely low concentrations. At the same time, they bind dissolved renin at low concentrations of from 1 to $3 \times 10^{-10}$. Interestingly, these monoclonal antibodies barely react with surface-bound renin. Accordingly, such monoclonal antibodies would not be detected in a customary primary screening based on the ELISA method. Group 4 comprises monoclonal antibodies that completely inhibit renin activity but that are approximately 1000-times weaker than monoclonal antibodies of group 3. In addition, they bind surface-bound renin (ELISA) and soluble renin (RIA) about equally well. The binding in an ELISA (at approximately $10^{-7}$M) is not, however, significantly different from that of non-specific monoclonal control antibodies.

5.3 Determination of the inhibition of rat and marmoset renin activity

In a manner analogous to that described in Example 5.1, the monoclonal antibody samples to be analysed are tested for inhibition of the activity of rat renin and of marmoset renin. For this purpose, however, untreated rat and marmoset plasma, i.e. rat and marmoset plasma containing normal amounts of angiotensinogen and renin, are used instead of the pre-treated human plasma.

None of the monoclonal antibodies listed in Table 1 inhibits rat renin.

The monoclonal antibodies R 3-27, R 3-36-16, R 3-47 and R 1-20 inhibit marmoset renin to the same extent as human renin (same IC 50 values). The determinant recognised by the corresponding monoclonal antibody is therefore identical or at least very similar in human renin and marmoset renin. Since the monoclonal antibodies R 3-36-16 and R 3-47 inhibit human renin very efficiently (Table 1), a homology of the catalytic site of the enzymes human renin and marmoset renin is indicated.

The monoclonal antibody R 1-19 inhibits the activity of marmoset renin at a concentration (IC 50) three times lower than that of human renin. This monoclonal antibody therefore reacts better with a molecule that has not been used for immunisation (Example 2.1).

The monoclonal antibody R 2-1 inhibits the activity of marmoset renin only at a concentration (IC 50) fifteen times higher than that of human renin. This monoclonal antibody therefore recognises a determinant that, although similar in marmoset and human renin, is not identical.

The purely partial inhibition of human renin observed in the case of the monoclonal antibodies R 3-21, R 2-1 and R 3-27 even at high concentrations (Table 1, last column) is found likewise also for marmoset renin.

EXAMPLE 6

Characterisation of the monoclonal antibodies

6.1 Determination of the antibody class

The class or subclass of the monoclonal antibodies produced by cloned hybridoma cells is determined in an ELISA. Microtitre plates are each coated with 1 μg of a rabbit immunoglobulin preparation of a class-specific or subclass-specific serum in 50 μl of PBS, free binding sites of the plate are saturated with RIA buffer (1% BSA in PBS, 0.2% NaN$_3$, pH 7.4) and the samples to be analysed are incubated in the wells for 1 hour at 37° C. After washing the plate, the bound monoclonal mouse antibodies are incubated for 1 hour at 37° C. with a preparation of phosphatase-labelled rabbit immunoglobulin of the serum preparation used for coating the plates, and the amount of enzyme taken up is determined as described in Example 4.1. The results are listed in Table 1.

6.2 Analysis of the amino acid sequence

The monoclonal antibodies are derivatised with 4-dimethylamino-4'-iodoacetamido-azobenzene, and heavy and light chains are separated by chromatography over a Sepharose®G 100 column. The fractions are eluted from the gel by electrodialysis and subjected to an amino acid sequence analysis in a Beckman 8906 sequencer in known manner [9].

The N-terminal amino acid sequence of the light chain of the monoclonal antibody R 3-36-16 (including the first hypervariable region in position 28-38) is as follows:

```
1                                    10
Asp—Asn—Val—Leu—Thr—Gln—Ser—Pro—Ser—Ser—

20
Leu—Ala—Val—Ser—Leu—(Arg)—Gln—(Arg)—Ala—Thr—

30
Ile—Ser—Cys—(Arg)—Ala—Ser—Glu—Ser—Val—(Asp)—

40
Ser—Tyr—Gly—Lys—X—Phe—Met—Y—Trp—Tyr.
```

Amino acids in parentheses are not known for certain. X and Y represent unspecified amino acids.

EXAMPLE 7

Determination of the cross-inhibition of the monoclonal antibodies

Microtitre plates are coated analogously to Example 4.1 with monoclonal antibodies of groups 1 to 3 (Table 1) in such a manner that approximately 150 ng of monoclonal antibodies are bound per well. 3 µg (20-fold excess) of the same monoclonal antibody or of a different monoclonal antibody from groups 1 to 3 are pre-incubated with 5 ng of $^{125}I$-labelled renin (Example 8.1) in 10 µl of solution for 15 hours at 4° C. or for 4 hours at 37° C., and then incubated in the wells of the coated microtitre plates for 2 hours at 37° C, and for 15 hours at 4° C. The plates are then washed and the bound renin is determined by measuring the radioactivity.

The results of this cross-inhibition experiment are given in Table 2. Binding of renin to a surface-bound monoclonal antibody is inhibited completely (more than 95% by pre-incubation with the same monoclonal antibody in solution (Table 2, diagonal). The monoclonal antibodies R 3-36-16 and R 3-47 inhibit each other completely and therefore recognise the same epitope on the renin molecule. The monoclonal antibody R 3-21 which cross-reacts with R 3-27 is likewise cross-inhibited by the monoclonal antibody R 3-17-7, but R 3-27 and R 3-17-7 do not have any effect on each other. These three monoclonal antibodies thus recognise partially overlapping, successive epitopes on the renin molecule. All the other monoclonal antibody pairings exhibit no reciprocal effect. These monoclonal antibodies therefore bind spatially separate epitopes on the renin molecule.

with 225 µl of RIA buffer (1% BSA in PBS, 0.2% NaN$_3$, pH 7.4).

50 µl in each case of a dilution series of a test solution or of the renin standard solution in RIA buffer containing 10% renin-free human plasma are introduced into the wells of the microtitre plates, 50 µl (80,000 cpm corresponding to 2.5 ng) of the solution of $^{125}I$-labelled renin from Example 8.1 are added in each case and incubation is carried out for 2 hours at 37° C. and for 15 hours at 4° C. The plates are washed with PBS and the radioactivity is measured. The concentration of human renin in the test solution is determined by a calibration curve generated with the standard solution.

In the same manner, microtitre plates are coated with a monoclonal antibody or with two monoclonal antibodies that recognise different epitopes (Table 2) and used for a single RIA.

8.3 Labelling of the monoclonal antibody R 3-36-16 with $^{125}I$

30 µg of monoclonal antibody R 3-36-16 are iodinated with $^{125}I$ (1 mC) and purified analogously to Example 8.1.

The monoclonal antibody R 3-27 is labelled in the same manner.

8.4 Determination of human renin by sandwich RIA

Analogously to Example 8.2, microtitre plates are coated with 150 µl of a solution of the monoclonal antibody R 3-27 (10 µg/ml) and protein-reactive sites are saturated. 50 µl in each case of a dilution series of a test solution (for example blood plasma of a patient) or of the renin standard solution in renin-free human plasma, 50 µl of RIA buffer and 50 µl (120,000 cpm

TABLE 2

| monoclonal antibody bound to titre plate | Cross-inhibition of the monoclonal antibodies inhibition of the binding to renin by excess monoclonal antibody | | | | | | |
|---|---|---|---|---|---|---|---|
| | R 2-12 | R 3-17-7 | R 3-21 | R 3-27 | R 2-1 | R 3-36-16 | R 3-47 |
| R 2-12 | +++ | − | − | − | − | − | − |
| R 3-17-7 | − | +++ | +++ | − | − | − | − |
| R 3-21 | − | ++ | +++ | + | − | − | − |
| R 3-27 | − | − | +++ | +++ | − | − | − |
| R 2-1 | − | − | − | − | +++ | − | − |
| R 3-36-16 | − | − | − | − | − | +++ | +++ |
| R 3-47 | − | − | − | − | − | +++ | +++ |

− 0–30% inhibition
+ 30–60% inhibition
++ 60–90% inhibition
+++ 95–100% inhibition

EXAMPLE 8

Radioimmunoassay (RIA) for the determination of human renin in plasma 8.1 Labelling of human renin with $^{125}I$ 10 µg of human renin from Example 1 are iodinated with $^{125}I$-sodium iodide (0.3 mC) and chloramine T according to the standard method of Greenwood and Hunter [10]. The reaction product is purified over an ion-exchange column Bio Rad AG ®1×8 and adjusted to an activity of 1.6×10$^6$ cpm/ml with PBS.

8.2 Determination of human renin by single RIA

Polyvinyl chloride microtitre plates (Dynatech Labs. Inc.) are coated by incubation with 100 µl of a solution in PBS, which contains 10 µg/ml each of monoclonal antibody R 2-1 and monoclonal antibody R 3-27, for 2 hours at 37° C. and for 15 hours at 4° C. The plates are washed with PBS and any protein-reactive sites still present are saturated by incubation for 2 hours at 37° C.

corresponding to 6 ng) of the solution of $^{125}I$-labelled antibody R 3-36-16 from Example 8.3 are incubated in the depressions of the microtitre plates for 2 hours at 37° C. and for 15 minutes at 4° C. The plates are washed with PBS and the radioactivity is measured. The concentration of human renin in the test solution is determined by a calibration curve (FIG. 1) generated with the standard solution.

The sensitivity of the test allows determination of as little as 1 pg of human renin in 50 µl of test solution (20 pg/ml). There is a linear dosage relationship in the entire range of from 1 to 100 pg of renin (50 µl of sample).

Human renin can also be determined in the same manner if, for example, monoclonal antibody R 2-1 or a mixture of R 2-1 and R 3-27 is used for coating the microtitre plates, or if the antibodies are exchanged for each other, that is to say the monoclonal antibody R 3-36-16 is used for the coating and, for example, the $^{125}$I-labelled monoclonal antibody R 3-27 is used for the development.

8.5 Test kit for a single RIA

A test kit for the single RIA described in Example 8.2 contains:

polyvinyl chloride microtitre plates
2 ml of solution of the monoclonal anti-human renin antibodies R 2-1 and R 3-27 (10 µg/ml of each)
100 ml of phosphate-buffered physiological saline solution (PBS)
100 MI of RIA buffer (1% BSA in PBS, 0.2% sodium azide)
2 ml of renin-free human plasma
2 ml of solution of $^{125}$I-labelled human renin of activity $1.6 \times 10^6$ cpm/ml
2 ml of standard solution containing 20 ng/ml human renin in renin-free human plasma
calibration curve 8.6 Test kit for sandwich RIA A test kit for the sandwich RIA described in Example 8.4 contains:

polyvinyl chloride microtitre plates
6 ml of solution of the monoclonal anti-human renin antibody R 3-27 (10 µg/ml)
100 ml of phosphate-buffered physiological saline solution (PBS)
100 ml of RIA buffer (1% BSA in PBS, 0.2% sodium azide)
2 ml of renin-free human plasma
2 ml of solution of $^{125}$I-labelled monoclonal anti-human renin antibody R 3-36-16 (Example 8.3) of activity $2.4 \times 10^6$ cpm/ml
2 ml of standard solution containing 20 ng/ml human renin in renin-free human plasma
calibration curve (FIG. 1)

EXAMPLE 9

Enzyme-immunoassay (ELISA) for the determination of human renin in plasma 9.1 ELISA with polyclonal anti-human renin serum Analogously to Example 8.2, microtitre plates are coated with 100 µl of a solution containing 10 µg/ml of monoclonal antibody R 3-36-16, and protein-reactive sites are saturated. The plates are incubated for 2 hours at 37° C. with 50 µl in each case of a dilution series of a test solution or of a renin standard solution in RIA buffer (1% BSA in PBS, 0.2% NaN$_3$, pH 7.4) containing 10% renin-free human plasma, are washed and are then incubated for 1 hour at 37° C. with 50 µl of a polyclonal rabbit-anti-human renin serum [11] that has been pre-diluted in a ratio of 1:500. After washing the plate, the bound rabbit antibodies are developed by incubation (1 hour at 37° C.) with a preparation of phosphatase-labelled goat-anti-rabbit immunoglobulin that has been pre-diluted in a ratio of 1:1000. Upon further incubation (30 minutes, 37° C.) with 100 µl of a solution of p-nitrophenyl phosphate (1 mg/ml in 10% diethanolamine buffer containing 0.5 mmol of MgCl$_2$, pH 9.8), the bound enzyme releases p-nitrophenol. By measuring the optical density at 405 nm, the amount of released p-nitrophenol is determined which is proportional to the amount of the bound enzyme phosphatase and hence proportional to the amount of human renin in the test solution.

Human renin can likewise be determined in the same manner if the monoclonal antibodies R 2-1 or R 3-27 or mixtures of two monoclonal antibodies are used for coating the microtitre plates.

9.2 Labelling of the monoclonal antibody R 3-36-16 with alkaline phosohatase 1.4 mg of the monoclonal antibody R 3-36-16 in 1.4 ml of PBS are coupled for 2 hours with a solution containing 5 mg of alkaline phosphatase (SIGMA P6774, type VII-T) according to the standard method of Voller et al. [12] using glutaraldehyde (0.2% v/v) and introduced into 5 ml of tris buffer 0.05M, pH 8.0, containing 1 mmol of MgCl$_2$, 1% BSA and 0.02% NaN$_3$. The solution is kept in the dark at 4° C.

9.3 ELISA with two different monoclonal antibodies

Polypropylene microtitre plates (Dynatech Labs. Inc.) are coated over a period of 2 hours at 37° C. with 150 µl of a solution of the monoclonal antibody R 3-27 (10 µg/ml) in a buffer pH 8.6 (carbonate-buffered 0.9% saline solution containing 0.02% sodium azide). The plates are washed five times with PBS and protein-reactive sites that are still present are saturated by incubation for 1 hour at 37° C. with 250 µl of RIA buffer (1% BSA in PBS, 0.2% NaN$_3$, pH 7.4). Plates coated in this manner can be kept at 4° C. in RIA buffer for a few days.

50 µl in each case of a dilution series of a test solution (for example blood plasma of a patient) or of the renin standard solution in renin-free human plasma, 50 µl of RIA buffer and 50 µl of a solution of the phosphatase-labelled antibody R 3-36-16 (Example 9.2) that has been diluted 1:100 with RIA buffer are mixed and incubated in the wells of the microtitre plates for 2 hours at 37° C. and for 30 minutes at 4° C. The plates are washed five times with PBS and the amount of enzyme bound after incubation (30 minutes, 37° C.) with 150 µl of a solution of p-nitrophenyl phosphate is determined as described in Example 9.1. The concentration of human renin in th test solution is calculated by a calibration curve (FIG. 2) generated with the standard solution.

The sensitivity of the ELISA allows the determination of less than 1 pg of human renin in 50 µl of test solution (20 pg/ml). There is a linear dosage relationship in the range of from 1 to 100 pg of renin (50 µl of sample).

9.4 Test kit for ELISA

A test kit for the ELISA described in Example 9.3 contains:

polypropylene microtitre plates,
6 ml of solution of the monoclonal anti-human renin antibody R 3-27 (10 µg/ml) in carbonate-buffered (0.072 g/l of Na$_2$CO$_3$ and 4.2 g/l of NaHCO$_3$) 0.9% saline solution containing 0.02% NaN$_3$,
100 ml of phosphate-buffered physiological saline solution (PBS),
100 ml of RIA buffer (1% BSA in PBS, 0.2 % NaN$_3$), 2 ml of renin-free human plasma,
0.2 ml of solution of alkaline phosphatase-labelled monoclonal anti-human renin antibody R 3-36-16 (Example 9.2) in tris buffer (0.05M, pH 8.0, 1 mmol of MgCl$_2$, 1% BSA, 0.02% NaN$_3$) of concentration 0.3 mg of antibody per ml,
10 ml of solution of p-nitrophenyl phosphate (1 mg/ml) in diethanolamine buffer (10% diethanolamine, 0.5 mmol of MgCl$_2$, 0.02% NaN$_3$, adjusted to pH 8.9 with HCl),
2 ml of standard solution containing 20 ng/ml human renin in renin-free human plasma,
calibration curve (FIG. 2), colour intensity scale for determining with the naked eye the amount of p-nitrophenol released.

EXAMPLE 10

Immuno-affinity chromatography for the purification of renin 10.1 Preparation of immuno-affinity gel Affi-Gel ®10 (Bio-Rad) is washed as directed by the manufacturer with cold distilled water and coupling buffer pH 8.0 (0.1M NaHCO$_3$ solution). A 50% strength suspension of the gel in coupling buffer (1 ml) is introduced into a plastics tube and mixed with the same volume of a purified monoclonal antibody solution that contains 10 mg of protein, and the mixture is rotated for 4 hours at room temperature. The gel is then washed with coupling buffer. In order to block the active sites that are still free, the gel is treated for 2 hours at room temperature with 0.1 ml of 1M ethanolamine-HCL (pH 8.0) per ml of gel, then washed with PBS (containing 10 mmol of sodium azide) and kept therein at 4° C. The degree of coupling is determined by measuring the optical density at 280 nm and is approximately 8 mg of monoclonal antibody per ml of gel.

b 10.2 Purification of marmoset or human renin

100 μl of an immuno-affinity gel prepared in accordance with Example 10.1 with the monoclonal antibody R 2-1 are incubated with 1 ml of kidney extract from marmosets (*Callithrix jacchus*) in a 5 ml Falkon tube for 30 minutes at room temperature with periodic shaking movements. The supernatant is removed, and the gel is washed with PBS and extracted with 1 ml of glycine hydrochloride buffer pH 3.0. The extracts are neutralised with tris buffer pH 8.5. In this manner, 70% (5–6 ng) of the renin present in the crude extract is obtained in pure form.

Human renin can be purified in the same manner.

Immuno-affinity gels containing the monoclonal antibodies R 3-21, R 1-19 or R 1-20 can be used in an analogous manner for the purification of human or marmoset renin.

EXAMPLE 11

Pharmaceutical preparation for parenteral administration 7.0 mg of monoclonal antibody R 3-36-16 prepared in accordance with Example 3 are dissolved in 20 ml of physiological saline solution. The solution is passed through a bacteriological filter, and the filtrate is portioned out and introduced under aseptic conditions into 10 ampoules. The ampoules each contain 0.7 mg of monoclonal antibody suitable for parenteral administration and are preferably stored at reduced temperature, for example at −20° C.

Literature references

[1] G. Köhler and C. Milstein, Nature 256, 495 (1975).
[2] D. Simon, F. X. Galen, C. Devaux, F. Soubrier, B. Pau, J. Ménard and P. Corvol, J. Clin. Endocr. Met. 53, 453 (1981).
[3] V. J. Dzau, D. Devine, M. Mudgett-Hunter, R. I. Kopelman, A. C. Barger and E. Haber, Clinical and Experimental Hypertension A5, 1207 (1983).
[4] F. Soubrier, T. T. Guyenne, M. F. Gonzales, P. Corvol and J. Ménard, in "Heterogeneity of Renin and Renin-Substrate" (ed. M. P. Sambhi), Elsevier North Holland Inc. 1981, page 237.
[5] D. R. Bangkan, I. Robertson, J. I. S. Robertson, C. J. Robinson and M. Iree, Clin. Sci. Mol. Med. 48, 135 (1975).
[6] B. Pau, D. Simon, F. X. Galen, C. Devaux, F. Soubrier, J. Ménard and P. Corvol, Clin. Sci. 61, 239 (1981).
[a] M. Shulman, C. D. Wilde and G. Köhler, Nature 276, 269 (1978).
[8] E. Engvall and P. Perlmann, J. Immunol. 109, 129 (1972).
[9] J.-Y. Chang. H. Herbst, R. Aebersold and D. G. Braun, Biochem. J. 211, 173 (1983).
[10] F. C. Greenwood, W. M. Hunter and J. S. Glover, Biochem. J. 89, 114 (1963).
[11] F. X. Galen, T. T. Guyenne, C. Devaux, C. Auzan, P. Corvol and J. Ménard, J. Clin. Endocr. Met. 48, 1041 (1979).
[12] A. Voller, D. E. Bidwell and A. Bartlett, Bull. World Health Organ. 53, 55 (1976).

We claim:

1. The monoclonal antibody R 3-36-16 an derivatives thereof.
2. The $^{125}$I-labelled derivative of the monoclonal antibody R 3-36-16 according to claim 1.
3. The derivative of themonoclonal antibody R 3-36-16 conjugated with alkaline phosphatase according to claim 1.
4. The hydridoma cell line designated R 3-36-16 which is deposited at the "Collection Nationale de Cultures de Microorganismes" of the Institut Pasteur in Paris under number I-253.
5. A test kit for the determination of human renin comprising a container with the monoclonal antibody R 3-36-16 and/or separate containers with derivatives thereof.
6. A test kit according to claim 5 for a radioimmunoassay further comprising a radioimmunoassay compatible carrier.
7. A test kit according to claim 5 for an enzyme-immunoassay further comprising an enzyme-immunoassay compatible carrier.
8. Pharmaceutical preparation for treating renin-induced high blood pressure, comprising an effective amount of the monoclonal antibody R 3-36-16 or of a derivative thereof together with a pharmaceutical carrier.
9. Method of treating a warm-blooded animal suffering from renin-mediated high blood pressure comprising administering to said animal a therapeutically effective amount of the monoclonal antibody R 3-36-16 or of a derivative thereof.
10. A method for the qualitative and/or quantitative determination of human renin comprising the steps of:
  (a) incubating a test sample with themonoclonal antibody R 3-36-16 or a derivative thereof, and
  (b) determining the presence or absence and/or the amount of the immune complex of human renin with the monoclonal antibody or the derivative thereof formed.
11. A method according to claim 10, characterized in that the amount of the immune complex in step (b) is determined by measuring the amount of a radioactive label.
12. A method according to claim 10, characterized in that the amount of the immune complex in step (b) is determined by measuring the amount of an enzyme label in an enzyme/substrate reaction.
13. A method for the purification of human renin by immuno-affinity chromatography on a carrier charged with the monoclonal antibody R 3-36-16 or a derivative thereof.

* * * * *